United States Patent [19]

Fischer et al.

[11] Patent Number: 4,703,014

[45] Date of Patent: Oct. 27, 1987

[54] KARL-FISCHER REAGENT AND PROCESS FOR THE DETERMINATION OF WATER

[75] Inventors: Wolfgang Fischer, Darmstadt; Karl-Dieter Krenn, Pfungstadt, both of Fed. Rep. of Germany

[73] Assignee: Merck Patent Gesellschaft mit beschrankter Haftung, Darmstadt, Fed. Rep. of Germany

[21] Appl. No.: 706,225

[22] Filed: Feb. 27, 1985

[30] Foreign Application Priority Data

Feb. 27, 1984 [DE] Fed. Rep. of Germany ....... 3407014

[51] Int. Cl.$^4$ ............................................. G01N 33/18
[52] U.S. Cl. ..................................... 436/42; 204/1 T
[58] Field of Search ................... 436/39, 42; 204/1 T, 204/1 M

[56] References Cited

U.S. PATENT DOCUMENTS

| | | |
|---|---|---|
| 2,967,155 | 1/1961 | Blomgren et al. . |
| 3,656,907 | 4/1972 | Delmonte . |
| 3,661,797 | 5/1972 | Meloan et al. . |
| 3,974,258 | 8/1976 | Poitevin et al. . |
| 4,005,983 | 2/1977 | Dahms . |
| 4,146,454 | 3/1979 | Haber . |
| 4,378,972 | 4/1983 | Scholz . |
| 4,385,124 | 5/1983 | Verbeek et al. . |
| 4,416,997 | 11/1983 | Fischer et al. ........................ 436/42 |
| 4,429,048 | 1/1984 | Scholz . |
| 4,550,083 | 10/1985 | Fischer et al. ........................ 436/42 |

FOREIGN PATENT DOCUMENTS

| | | |
|---|---|---|
| 3008421 | 3/1980 | Fed. Rep. of Germany . |
| 3039511 | 10/1980 | Fed. Rep. of Germany . |
| 728947 | 4/1955 | United Kingdom . |

OTHER PUBLICATIONS

Anal. Chim. Acta 94, 395 (1977).

Primary Examiner—Barry S. Richman
Assistant Examiner—Robert J. Hill, Jr.
Attorney, Agent, or Firm—Millen & White

[57] ABSTRACT

A Karl-Fischer reagent useful in a process for the determination of water contains a pyridine substitute, sulfur dioxide and iodine. As the pyridine substitute, the reagent contains at least one compound from the group comprising the guanidines, amidines, imido-esters, isoureas, cyanamide, or salts thereof with a weak organic acid.

12 Claims, No Drawings

KARL-FISCHER REAGENT AND PROCESS FOR THE DETERMINATION OF WATER

BACKGROUND OF THE INVENTION

This invention relates to a modified Karl-Fischer reagent for the determination of water, the reagent containing a pyridine substitute, sulfur dioxide and iodine, and to a process for the determination of water by means of this reagent.

A number of proposals for the replacement of pyridine in the Karl-Fischer reagent by other substances are known from the literature. In Anal. chim. Acta 94, 395 (1977), sodium acetate is used as a substitute for pyridine. However, this substitution involves certain disadvantages. For example, ethyl acetate forms by reaction with the alcohol used as the solvent, water being eliminated which naturally interferes in a method for the determination of water. The solutions are therefore unstable, and their blank value increases continuously.

In British Pat. No. 728,947, alcoholates, phenolates and metal salts of weak organic acids are also mentioned in addition to acetates as a substitute for pyridine. A check of the substances mentioned in the patent specification showed that these are unsuitable as a pyridine substitute, in some case due to inadequate solubility and in other cases due to insufficient stability of the finished solutions.

To overcome these disadvantages, attempts have been made very recently to replace pyridine by aliphatic amines in a defined molar ratio relative to sulfur dioxide, or by heterocyclic compounds (European Pat. No. 35,066; U.S. Pat. Nos. 4,429,048 and 4,378,972). However, even this pyridine substitute still has disadvantages, because the stability of the end point fluctuates with the quantity of the water to be titrated.

SUMMARY OF THE INVENTION

Accordingly, it is an object of this invention to provide a modified Karl-Fischer reagent which is stable, gives exact analytical results and shows an end point which is as stable as possible even in the case of a variable quantity of water.

Upon furthe rstudy of the specification and appended claims, further objects and advantages of this invention will become apparent to those skilled in the art.

Surprisingly, it has been found that such a Karl-Fischer reagent can be obtained when a compound from the group comprising the guanidines, amidines, imidoesters, isoureas and/or cyanamide or salts thereof with a weak organic acid, preferably an aromatic carboxylic acid, is used in the known Karl-Fischer reagents in place of pyridine or other nitrogenous heterocyclic compounds or amines.

These substances are very readily soluble in the reagent solution, virtually do not react with alcohols to form esters, are very stable on storage and show stable end points even in titration over a wide range of water.

An additional use of acids in the Karl-Fischer reagent is mentioned in European Pat. No. 35,066 and its U.S. counterparts, but the acids listed there do not give salts usable for the reagent according to this invention (if sulfuric acid or hydriodic acid is used) or the reagent is rendered unstable by the addition of acid (if formic acid, oxalic acid or acetic acid is used).

The invention relates to a Karl-Fischer reagent for the determination of water, which contains a pyridine substitute, sulfur dioxide and iodine and which is characterized in that at least one compound from the group comprising the guanidines, amidines, imido-esters, isoureas, cyanamide or salts thereof with a weak organic acid is present as the pyridine substitute.

The invention also relates to a process for the determination of water by means of the Karl-Fischer reagent.

DETAILED DISCUSSION

The Karl-Fischer reagent according to the invention comprises two solutions, namely a dissolver and a titrating agent, or a so-called single-component reagent which contains all the constituents in a single solution. The dissolver contains sulfur dioxide and the pyridine substitute in a solvent and is used to take up the sample which is to be examined for its water content. The titrating agent is a solution of iodine, standardized to a constant titer, in a solvent.

As already mentioned, however, the dissolver and titrating agent cn also be present as a single-component reagent. This is sufficiently stable for use as a titrating liquid in the conventional manner. The single-component reagent is of particular advantage whenever the substance to be examined is more readily soluble in a solvent other than that contained in the dissolver. In this case, the reaction rate is moreover independent of the dissolution rate.

Suitable pyridine substitutes according to the invention include:

guanidine derivatives, e.g., mono-, di-, tri and tetra-$C_1$-6-alkylguanidines, as well as salts thereof with weak acids such as benzoic acid, salicylic acid and the like;

amidines, e.g., benzamidine, acetamidine and $C_{1-6}$-alkylamidines in general, the nitrogen atoms of which can be substituted by $C_{1-6}$-alkyl groups, and the mentioned salts thereof;

imido-esters such as 2-$C_1$-6-alkyloxazoline ($\Delta^2$), preferably 2-methyloxazoline, 2-ethyloxazoline, 2-propyloxazoline or 2-phenyloxazoline;

isoureas, e.g., 0-$C_1$-6-alkylisourea, e.g., 0-methylisourea, 0-ethylisourea and 0-propylisourea, and cyanamide.

Weak acids suitable for forming salts with these compounds include, for example, hydrocarbon aromatic carboxylic acids, such as benzoic acid, its 2-mono-$C_1$-6-alkyl or 2,6-di-$C_1$-6-alkyl derivatives, in particular the methyl and ethyl derivatives, and salicylic acid and analogous derivatives thereof. In general aromatic weak acids will be suitable for salt formation as long as they are compatible with the Karl-Fischer systems and have pka's of about >2.

The salts have the advantage that, in addition to their action as a base, they also have an action buffering the reaction medium. This is important in particular in an acidic or basic medium, because the use of free bases having a weaker buffer action gives unusable results even at low water contents of the sample.

The pyridine substitute of the invention is, of course, functionally equivalent to pyridine in a Karl-Fischer reagent and method. Thus, it will have the necessary solubility and basicity properties and will be otherwise compatible with the other components in the reagent and with the details of its use.

Guanidinium benzoate, tetramethylguanidine, benzamidine, benzamidinium benzoate, acetamidine, acetamidinium benzoate, N-phenyl-N',N'-dimethylacetamidine, 0-methylisourea salicylate, 2-methyloxazoline and cyanamide are particularly preferred for use in the reagent according to the invention.

The molar ratio of the compound according to the invention and sulfur dioxide is generally in the range from 0.5:1 to 3:1, preferably from 1:1 to 1.5:1.

Suitable solvents for both the dissolver and for the titrating agent are all the solvents described in the literature for this purpose, preferably alcohols and/or glycols, in particular lower alcohols (e.g., of one to about six C-atoms) such as methanol, ethanol, propanol and the like, as well as ethylene glycol and ethylene glycol monoalkyl ether (e.g., where alkyl is of 1–6 C-atoms), and also chloroform. The solvents can be used singly or in any desired mixing ratio. Thus, for example, it is possible to dissolve the pyridine substitute according to the invention in an alcohol or in a glycol or in a mixture of any desired ratio of alcohols, glycols or mixtures of both types of solvent, to add the required quantity of sulfur dioxide and, in the case of the so-called single solution, also to add iodine as well.

The use of the pyridine substitutes according to the invention gives a number of advantages: the transition at the equivalence point is clearer and more stable than in the cse of the conventional Karl-Fischer reagents; the reagent has a higher solubility and hence a greater range of application, and altogether it is non-polluting and inexpensive.

When the Karl-Fischer reagent according to the invention is used, the end point of the titrimetric water determination cn be detected visually, photometrically or electrometrically (dead stop method), coulometric method). The reagent is suitable for use both in automatic titrators and for methods used in the field. When used in the field, it is advisable to replace the methanol by the low-vapor pressure solvents mentioned. The titration is generally carried out while atmospheric moisture is excluded. Electrometric titration, in particular the so-called dead stop method, is preferred nowadays.

Unless indicated otherwise herein, the details of the reagent and method of this invention are fully conventional including relative amounts of $SO_2$, $I_2$ and solvent and manipulative details. ("Aquametry", J. Mitchell, D. M. Smith; 1980, J.Wiley & Sons, New York, Chichester, Brisbane, Toronto)

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

A. Two-component reagents

EXAMPLE 1

To prepare the dissolver and the titrating agent, the particular substances are dissolved in the appropriate solvent:
 (a) Dissolver:
272 g of guanidinium benzoate (1.5M) and 64 g of sulfur dioxide (1M) in 1 l of methanol
 (b) Titrating agent:
85 g of iodine in 1 l of methanol The substance to be examined for its water content is dissolved, depending on the estimated water content, in 20 ml of the dissolver and titrated with the titrating agent ot the end point, with continuous stirring and exclusion of atmospheric moisture. The results were in accordance with that obtained with conventional pyridine containing Karl-Fischer reagents.

EXAMPLE 2

The following Karl-Fischer solutions are prepared:
 (a) Dissolver:
173 g of tetramethylguanidine (1.5M) and
96 g of sulfur dioxide (1.5M) in
1 l of ethanol
 (b) Titrating agent:
85 g of iodine in 1 l of ethanol With these solutions, the same results as with the solutions according to Example 1 are obtained. The results also do not change after partial or complete replacement of the ethanol by ehtylene glycol monomethyl ether.

EXAMPLE 3

The following Karl-Fischer solutions are prepared:
 (a) Dissolver:
160 g of N-phenyl-N',N'-dimethylacetamidine (1M) and
60 g of sulfur dioxide (0.94M) in
1 l of methanol
 (b) Titrating agent:
85 g of iodine in 1 l of methanol With these solutions, the same results as with the solutions according to Examples 1 and 2 are obtained.

EXAMPLE 4

The following Karl-Fischer solutions are prepared:
 (a) Dissolver:
77 g of benzamidine (1.5M) is dissolved in
1 l of methanol and
32 g of sulfur dioxide (0.5M) is introduced, with stirring.
 (b) Titrating agent as in Example 3.

With this reagent, the analytical results obtained are analogous to those with the reagent according to Example 1.

EXAMPLE 5

The following Karl-Fischer solutions are prepared:
 (a) Dissolver:
182 g of benzamidinium benzoate (1M) is suspended in
1 l of methanol and
38 g of sulfur dioxide (0.6M) is introduced, with stirring.
 (b) Titrating agent as in Example 3.

This reagent also gives results analogous to that according to Example 1.

EXAMPLE 6

The following Karl-Fischer solutions are prepared:
 (a) Dissolver:
63 g of cyanamide (1.5M) is dissolved in
1 l of methanol and
96 g of sulfur dioxide (1.5M) is introduced, with stirring.
 (b) Titrating agent as in Example 3.

This reagent can be used only after standing for several days, and it gives excellent analytical results.

B. Single-component reagents

EXAMPLE 7

A single-component solution is prepared from
543 g of guanidinium benzoate (3M),
128 g of sulfur dioxide (2M) and
160 g of iodine in
1 l of ethylene glycol monomethyl ether The substance to be examined for its water content is dissolved in 20 ml of a solvent and titrated with the single-component solution. 1 ml of this solution is equivalent to 5.4 mg of water.

EXAMPLE 8

A single-component solution is prepared from
259 g of tetramethylguanidine (2.25M),
128 g of sulfur dioxide (2M) and
160 g of iodine in
1 l of ethylene glycol monomethyl ether The substance to be examined for its water content is dissolved in 20 ml of a solvent and titrated with the single-component solution. 1 ml of this solution is equivalent to 5.5 mg of water.

EXAMPLE 9

A single-component solution is prepared by suspending
485 g of benzamidinium benzoate (2.7M) in
1 l of ethylene glycol monomethyl ether.
128 g of sulfur dioxide (2M) is introduced, with stirring, and
62.5 g of iodine is then added.

The determination is carried out analogously to Example 6. The factor of this solution is 3.0, that is to say 1 ml of the solution indicates 3 mg of water.

EXAMPLE 10

A single-component solution is prepared from
175 g of acetamidine (3M),
128 g of sulfur dioxide (2M) and
170 g of iodine in
1 l of ethylene glycol monomethyl ether.
The factor of this solution is 5.7.

EXAMPLE 11

A single-component solution is prepared from
542 g of acetamidinium benzote (3M),
113 go of sulfur dioxide (1.77M) and
170 g of iodine in
1 l of ethylene glycol monomethyl ether.
The factor of this solution is 5.3.

EXAMPLE 12

A single-component solution is prepared from
637 g of 0-methylisourea salicylate (3M),
128 g of sulfur dioxide (2M) and
160 g of iodine in
1 l of ethylene glycol monomethyl ether.
The factor of this solution is 5.3.

EXAMPLE 13

A single-component solution is prepared from
637 g of 0-methylisourea salicylate (3M),
64 g of sulfur dioxide (1M) and
80 g of iodine in
1 l of ethylene glycol monomethyl ether.
The factor of this solution is 3.0.

EXAMPLE 14

A single-component solution is prepared from
255 g of 2-methyloxazoline (3M),
190 g of sulfur dioxide (3M) and
170 g of iodine in
1 l of ethylene glycol monomethyl ether.
The factor of this solution is 5.8.

C. Coulometric reagents

EXAMPLE 15

To carry out a coulometric determination of water, the following solutions are used:
(a) Cathode solution:
272 g of guanidinium benzoate (1.5M) and
64 g of sulfur dioxide (1M) are dissolved in a mixture of
0.7 l of methanol and
0.3 l of chloroform.
(b) Anode solution:
Analogous to (a), but with the addition of 6 g of iodine.

EXAMPLE 16

The following solutions are prepared:
(a) Cathode solution:
173 1 g of tetramethylguanidine (1.5M) and
96 1 g of sulfur dioxide (1.5M) in
0.7 l of methanol and
0.3 l of chloroform.
(b) Anode solution:
Analogous to (a), but with the addition of 6 g of iodine.

EXAMPLE 17

The following solutions are prepared:
(a) Cathode solution:
160 g of N-phenyl-N',N'-dimethylacetamidine (1M) and
60 g of sulfur dioxide (0.94M) in
1 l of methanol.
(b) Anode solution:
Analogous to (a), but with the addition of 6 g of iodine.

EXAMPLE 18

The following solutions are prepared:
(a) Cathode solution:
Analogous to the dissolver according to Example 4.
(b) Anode solution:
Analogous to (a), but with the addition of 6 g of iodine.

EXAMPLE 19

The following solutions are prepared:
(a) Cathode solution:
Analogous to the dissolver according to Example 5.
(b) Anode solution:
Analogous to (a), but with the addition of 2 g of iodine.

EXAMPLE 20

The following solutions are prepared:
(a) Cathode solution:
Analogous to the dissolver according to Example 6.
(b) Anode solution:
Analogous to (a), but with the addition of 2 g of iodine.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a Karl-Fischer reagent useful for the determination of water, comprising a solution containing a pyridine substitute, sulfur dioxide and iodine, the improvement wherein the pyridine substitute is at least one compound which is a salt of a mono-, di-, tri-, or tetra-alkyl $C_1$-6 guanidine derivative or guanidine with benzoic acid or a 2-$C_1$-6-alkyl- or 2,6-di-$C_1$-6-alkyl benzoic acid, said pyridine substitute being functionally equivalent to pyridine in a Karl-Fischer reagent.

2. A reagent of claim 1 wherein the ratio of sulfur dioxide to said pyridine substitute is 0.5:1 to 3:1.

3. A Karl-Fischer reagent of claim 1 wherein said salt is a benzoic acid salt.

4. A Karl-Fischer reagent of claim 1 wherein said pyridine substitute is a guanidinium salt.

5. A Karl-Fischer reagent of claim 4, wherein said guanidinium salt is guanidinium benzoate.

6. A method for the determination of water in a sample, comprising dissolving the sample in a solvent to form a solution and titrating the solution with the Karl-Fischer reagent of claim 1.

7. A method of claim 6 wherein the titrating is carried out with electrometric end point detection.

8. In a Karl-Fischer reagent system useful for the determination of water comprising a first solution which functions as a dissolver and which comprises sulfur dioxide, a pyridine substitute and a compatible solvent, and second solution which functions as a titrating agent and which comprises iodine and a comptible solvent, the improvement wherein said pyridine substitute is a salt of a mono-, di-, tri-, tetra-$C_1$-6-alkyl guanidine derivative, or guanidine with benzoic acid or a 2-$C_1$-6-alkyl- or 2,6-di-$C_1$-6-alkyl benzoic acid.

9. A reagent of claim 8 wherein the solvent in the first or the second solution is methanol or ethylene glycol monomethyl ether.

10. A method for the determination of water in a sample, comprising dissolving the sample in the dissolver of claim 8 to form a solution and titrating the solution with the titrating agent of claim 8.

11. A Karl-Fischer reagent comprising a Karl-Fischer reagent solvent in which is dissolved sulfur dioxide, iodine, a pyridine substitute and essentially no pyridine, the pyridine substitute being at least one compound which is a salt of guanidine with benzoic acid or a 2-$C_1$-6-alkyl-or 2,6-di-$C_1$-6-alkyl benzoic acid, said pyridine substitute being functionally equivalent to pyridine in a Karl-Fischer reagent.

12. A Karl-Fischer dissolver solution for use in a Karl-Fischer reagent, said dissolver solution consisting essentially of sulfur dioxide and at least one compound which is a salt of a guanidine with benzoic acid or a 2-$C_1$-6-alkyl-or 2,6-di-$C_1$-6-alkyl benzoic acid, said at least one compound being functionally equivalent to pyridine in a Karl-Fischer dissolver solution.

* * * * *